United States Patent [19]

Landau et al.

[11] Patent Number: 4,692,157

[45] Date of Patent: Sep. 8, 1987

[54] SQUEEZE-ACTUATED SYRINGE WITH POSITION-SELECTABLE LOCK

[75] Inventors: Boris Landau, Huntington Beach; Marius Saines, Los Angeles, both of Calif.

[73] Assignee: Ergomed, Huntington Beach, Calif.

[21] Appl. No.: 812,773

[22] Filed: Dec. 23, 1985

Related U.S. Application Data

[63] Continuation-in-part of Ser. No. 695,457, Jan. 28, 1985, Pat. No. 4,581,021.

[51] Int. Cl.$^4$ .............................................. A61M 5/18
[52] U.S. Cl. .................................................... 604/214
[58] Field of Search ............... 604/214, 212, 232, 187; 222/96, 103

[56] References Cited

U.S. PATENT DOCUMENTS

| | | |
|---|---|---|
| 798,093 | 8/1905 | Dean . |
| 1,222,814 | 4/1917 | Storz ................................ 604/214 X |
| 1,880,354 | 10/1932 | Mueller . |
| 1,961,489 | 6/1934 | Hein ................................... 128/232 |
| 2,534,708 | 12/1950 | Goodheart .......................... 222/103 |
| 2,618,263 | 11/1952 | Lakso et al. ....................... 128/216 |
| 2,763,401 | 9/1956 | Buras, Jr. ........................... 222/103 |
| 2,781,951 | 2/1957 | Hanford ............................. 222/103 |
| 3,099,264 | 7/1963 | Hubbard ............................. 128/215 |
| 3,114,369 | 12/1963 | Hall ..................................... 128/216 |
| 3,332,579 | 7/1967 | Peters ................................... 222/96 |
| 3,768,699 | 10/1973 | Robe, Jr. ............................. 222/103 |
| 4,013,073 | 3/1977 | Cunningham ...................... 128/216 |
| 4,432,768 | 2/1984 | Brown et al. ....................... 604/200 |
| 4,475,906 | 10/1984 | Holzner ............................... 604/212 |
| 4,581,022 | 4/1986 | Leonard et al. .................... 604/224 |

FOREIGN PATENT DOCUMENTS

| | | | |
|---|---|---|---|
| 548625 | 11/1957 | Canada ............................... | 222/103 |
| 1030639 | 6/1953 | France . | |

*Primary Examiner*—John D. Yasko
*Attorney, Agent, or Firm*—Klein & Szekeres

[57] ABSTRACT

A squeeze-actuated syringe includes a longitudinal body adapted to receive a collapsible ampul. A handle is attached by a hinge to one end of the body, the other end of which is adapted to receive a fitting on the ampul. The handle has a projection or pad on its underside in opposed relationship to the ampul received in the body. When the handle is squeezed toward the body, the ampul is compressed, discharging its contents through a hypodermic needle or the like attached to the fitting. A ratcheting lock mechanism on the handle and the body defines a plurality of selectable detented positions for the handle relative to the body. The handle can be stopped at any selected detented position, thereby allowing the contents of the ampul to be discharged in intermittent stages. In one embodiment, the ratcheting lock mechanism comprises a first serrated member on the body which is co-engageable with a second serrated member on the handle. In a second embodiment, the body carries a pair of laterally-opposed serrated members which are engageable by lateral flanges on the handle. In both embodiments, the ratcheting lock mechanism can be disengaged by flexing one or both of the serrated members. The invention can be used for aspiration by using an evacuated or empty ampul, and by gradually or intermittently lifting the handle off of the ampul using the ratcheting lock mechanism.

22 Claims, 16 Drawing Figures

SQUEEZE-ACTUATED SYRINGE WITH POSITION-SELECTABLE LOCK

CROSS-REFERENCE TO RELATED APPLICATION

This application is a Continuation-In-Part of co-pending Application Ser. No. 695,457, Filed Jan. 28, 1985, now U.S. Pat. No. 4,581,021.

BACKGROUND OF THE INVENTION

This invention relates generally to the field of medical syringes used for injecting a medicinal liquid into a patient. More specifically, it relates to a syringe adapted for use with a disposable hypodermic needle and a compressible ampul that is either pre-filled with a medicinal liquid, or empty (or evacuated) for filling with a bodily fluid extracted from the patient.

Conventional hypodermic syringes comprise a tubular reservoir with a fitting at one end for the attachment of a hypodermic needle. The other end of the reservoir is provided with a plunger. Syringes of this type must be filled from a separate vial or ampul in the well-known manner of pushing the plunger all the way into the reservoir, inserting the needle into the vial, and pulling the plunger out until the reservoir is filled to the desired level, as indicated by volumetric markings on the reservoir wall. Before injection, a small amount of liquid must be expressed through the needle to assure that no air is injected.

Several disadvantages of these conventional syringes have been recognized. For example, the need to fill the syringe from a separate vial is cumbersome and time-consuming, as is the need precisely to measure the dosage and then express the liquid to remove air from the syringe. Also, the plunger mechanism can be awkward to manipulate in certain situations, and, in any case, requires at least some degree of dexterity. This can present a problem in certain applications, such as in the application of local anesthesia, where an injection must be made into a relatively inaccessible part of the body. Patients, such as diabetics, who must perform self-injections, and particularly those who are elderly, weak, or infirm, sometimes find it difficult to inject themselves with the plunger-type syringe.

The awkwardness of plunger-type syringes also makes them inconvenient to use to withdraw a bodily fluid from a patient, such as when a blood sample is taken from a vein. This awkwardness had led to the development of alternative devices for collecting blood samples. One of the most popular of such devices comprises an evacuated test tube sealed with a rupturable stopper. The tube is used in conjuction with a holder which comprises a cylindrical body having an open end and a closed end fitted with a double-pointed hypodermic needle. The needle has an interior portion extending axially into the interior of the holder, and an exterior portion adapted for insertion into a vein. To use this type of device, the exterior point of the needle is inserted into the vein, and then the tube is inserted into the holder, stoppered-end first, whereby the interior point of the needle ruptures the stopper, thereby allowing blood to be drawn from the vein in response to the reduced pressure inside the evacuated tube.

While the evacuated type device is more convenient to use than a plunger-type syringe for taking blood samples and the like, it does suffer certain drawbacks. For example, the insertion of the tube into the holder so as to rupture the stopper must be done carefully to avoid excessive movement of the needle in the vein, which could cause injury to the vein. Also, there is a reduced degree of manual control by the practitioner over the rate of blood withdrawal. This is a result of a fixed pressure differential being applied to the vein once the stopper is ruptured. In some cases, such as in the veins of infants or in veins weakened by disease, the pressure differential applied to the vein could be excessive, with possible vein collapse or tissue withdrawal resulting. In addition, occasional problems have been noted with contamination of the blood sample with the lubricant used to provide an air-tight seal around the stopper, or with the material of the stopper itself. Finally, a pipette must be used to extract multiple specimens ("aliquots") from the tube, thereby providing additional opportunities for contamination of the collected sample.

Accordingly, attempts have been made to provide alternative syringe designs which overcome the disadvantages of the plunger mechanism. One approach has been to provide a syringe with a self-contained reservoir or ampul pre-filled with a precisely measured amount of medicament. The ampul has flexible walls, so that its contents can be discharged by compressing or squeezing it. Devices of this type are exemplified in the following U.S. patents:

| Patent No. | Patentee |
| --- | --- |
| 798,093 | Dean |
| 1,222,814 | Storz |
| 2,618,263 | Lakso, et al. |
| 3,099,264 | Hubbard |
| 3,114,369 | Hall |
| 4,013,073 | Cunningham |
| 4,475,906 | Holzner |

While the above-listed prior art devices do, in varying degrees, avoid the aforementioned problems associated with the plunger-type syringe, none has found widespread acceptance by medical practitioners, for a variety of reasons. For example, some of the prior art devices offer insufficient physical support for the needle during injection, making their use awkward at best. Others require a degree of dexterity in their use that, while possibly an improvement over the plunger-type syringe, still renders them ill-suited for self-injection, especially by the physically feeble. Another drawback in some prior art devices is their inability to be used with disposable needles. In such devices, the syringe and needle are manufactured as a disposable unit, a practice some may consider wasteful. Also, in devices of this type some mechanism must be included to prevent the flow of liquid from the reservoir into the needle until an injection is to be performed. Such a mechanism adds to the complexity, and thus the cost, of such devices.

Still another shortcoming in the prior art discussed above is the difficulty in injecting only a portion of the ampul's volume. Specifically, once the ampul is partially squeezed to discharge a portion of its contents, any relaxation of the pressure applied to the ampul may allow the ampul to return to its original shape, due to the resilience or "shape memory" of the ampul's material, or due to back pressure experienced through the needle. The result could be the introduction of air into the ampul, or, if the needle has been kept inserted in the patient's body, the aspiration of tissue into the syringe. Even if the ampul is constructed to minimize the risk of air or tissue aspiration, such syringes lack any convenient means for the practitioner to "meter" measured portions of the ampul's contents over a period of time, as is frequently done in administering a local or spinal anesthetic. Thus, in short, squeeze-actuated syringes of the prior art have been "one-shot" devices, in which the entire volume of the ampul is advantageously injected by a single, continuous squeeze of the syringe, rather than intermittently, over a period of time.

There has thus been a long-felt, but not entirely satisfied, need for a syringe that contains a pre-measured reservoir or ampul of medicament, which provides good physical support for the needle and which offers an injection mechanism that is easy to manipulate without much dexterity or strength. The need has also been felt for a syringe of this nature which can use disposable needles, and which, therefore, does not require means for blocking flow from the reservoir into a pre-attached needle. In addition, there has been a need for a syringe that can be easily adapted for use as an aspirating syringe to collect bodily fluids from a patient, especially venous blood samples. Moreover, there has been a further need for a syringe having the aforementioned characteristics, which also allows for convenient metering of the syringe contents intermittently over a period of time.

SUMMARY OF THE INVENTION

Broadly, the present invention is a squeeze-actuated syringe having a ratcheting lock mechanism that provides a plurality of selectable, detented positions for the injection mechanism. More specifically, the syringe includes a rigid body that provides both a stationary grip and an open receptacle for a collapsible ampul. The body has a proximal end and a distal end, with pressure application means being operatively connected to the distal end. The pressure application means is in the form of a squeeze-actuated handle that is connected by a double-jointed or multi-jointed (arcuate) hinge to the distal end of the body. The handle and the body are thus configured to be gripped in a person's hand, and the handle squeezed toward the receptacle to bring pressure to bear against the ampul seated therein. The body has a fitting at its proximal end which receives a mating fitting at the proximal end of the ampul. The ampul fitting, in turn, is adapted for the attachment of a hypodermic needle or the like. The needle is of the double-ended type, having an inner or distal end that passes through the ampul fitting and into the ampul, thereby allowing the contents of the ampul to be discharged through the needle as the ampul is compressed by the handle being urged against it. Alternatively, if the ampul has been previously evacuated, bodily fluid, such as venous blood, can be aspirated through the needle into the ampul as the handle is lifted away from the body.

The ratcheting lock mechanism is engageable between the handle and the body This mechanism defines a plurality of selectable positions for the handle relative to the body, and releasably locks the handle into any selected one of the positions. In this manner, as the handle is pressed downwardly to compress the ampul, it can be stopped and releasably locked in a selected position in which the ampul is only partially emptied, thereby allowing the administration of the contents of the ampul to be metered in measured units over a period of time, as opposed to having the entire contents administered at once. In the aspiration mode, the handle can be lifted from the ampul gradually, or it can be stopped and releasably locked in selected positions as it is lifted away from the ampul, allowing a controlled modulation of the aspiration procedure.

In a first preferred embodiment, the lock mechanism comprises a a first serrated member extending from the body approximately transversely to the body's longitudinal axis, and a second serrated member extending from the handle approximately transversely to the handle's longitudinal axis. Each of the aforesaid selectable positions is defined by a serration on the first serrated member. The two serrated members are aligned with their respectives serrations or teeth in slidable co-engagement, with the teeth of the second serrated member successively engaging the teeth of the first serrated member as the handle is moved toward the body. In this manner, the selectable positions defined by the first serrated member are detented, whereby the motion of the handle can be stopped at each position before continuing downwardly toward the body. The teeth on the two serrated members are sloped so as to provide a ratcheting action. That is, the handle can be moved through successive detented positions as it is urged toward the body, but, when released, the handle is restrained from movement away from the body. In this manner, metered portions of the ampul's contents can be intermittently injected, with substantially reduced risk of aspirating tissue or air into the ampul through the needle. When the injection has been completed, one of the serrated members is resiliently flexed away from the other, thereby disengaging their teeth, and allowing the handle to be lifted away from the body.

In a second preferred embodiment, a pair of serrated members extend from opposite sides of the body, near its proximal end, in a direction approximately transverse to the longitudinal axis of the body. The teeth of the two serrated members face each other across the interior surface of the body, in lateral opposition to each other. Each selectable position is defined by an opposed pair of serrations. The handle extends between the two serrated members, and each side of the handle has a flange, or lip, that is engageable with the teeth of the adjacent serrated member. The two serrated members are flexible, and they are joined across their top ends by a flexible bridge. This structure provides a detented, ratcheting action for the handle, similar to that of the first embodiment, when the handle is urged downwardly (i.e., toward the ampul seated in the body). The handle can be released to be lifted away from the body by pressure applied to the top of the bridge. This pressure bows the two serrated members outwardly away from each other, thereby disengaging their teeth from the flange or lip of the handle.

In this second embodiment, as in the first embodiment, the handle can be connected to the body by a double jointed hinge. Alternatively, a multi-jointed (i.e., arcuate) hinge can be used. In either case, the longitudinal axis of the handle is maintained substantially parallel to the longitudinal axis of the body as the handle is moved toward and away from the body.

With either embodiment, modulated and controlled aspiration can easily be accomplished. Aspiration (such as withdrawing blood from a vein) can be accomplished using a previously-evacuated ampul (either evacuated and sealed during manufacture, or evacuated by full compression of the handle to collapse the ampul in the syringe body). The needle having been inserted into the patient's body (in a selected vein, for example,) the handle is controllably lifted to allow a modulated withdrawal of bodily fluid into the ampul by appropriate manipulation of the ratchet release mechanism (i.e., the mechanism by means of which the handle is disengaged from teeth of the serrated member or members attached to the body).

Also, with either embodiment, a compound handle can be employed to allow greater force to be applied against the ampul. This is advantageous when the medicament to be injected from the ampul has a relatively high viscosity, or where the fluid from the ampul must be injected at a relatively high pressure, such as in angioplasty.

The present invention offers significant advantages over prior art syringes. Of key importance is the squeeze action by which the injection is performed. The mechanism which squeezes the ampul to discharge its contents requires little strength or dexterity for actuation, making it highly advantageous for use by weak or infirm patients who must inject themselves with medication. This feature is also advantageous for injections that must be made into relatively inaccessible parts of the body.

Another advantageous feature of the invention is its use of pre-filled ampuls containing pre-measured doses of medication. This eliminates the need to fill the syringe reservoir from a separate vial before injection, thereby not only saving time, but also providing a more accurately measured dosage. The action of the handle in compressing the ampul also provides a uniform flow through the needle with considerably less conscious effort than is required with the plunger-type syringe.

Another advantage enjoyed by the present invention is that it can accommodate, in a single syringe body, ampuls of widely varying volumetric capacities, and even large volumes can be injected with good flow rate uniformity, with substantially less physical effort than is required with plunger-type syringes. Enhancing the ability to provide low-effort injection with good flow control is the rigid support for the needle provided by the body and the needle attachment fitting.

Significant advantages are also afforded by the ratcheting action of the handle. For example, as mentioned above, intermittent injections of metered fractions of the contents of the ampul can be performed with a minimal risk of aspiration of air or tissue. In addition, when used in the aspiration mode to draw blood samples and the like, the rate fluid withdrawal can be conveniently modulated. Moreover, the aspiration can be performed with a minimum of needle movement in the patient's body. Once withdrawn into the ampul, the blood or other bodily fluid can be extracted in multiple aliquots from the ampul without a pipette or other implement, thereby minimizing the risk of contamination.

As will be best appreciated from the detailed description which follows, these and other advantages which will be made apparent overcome the aforementioned problems associated with prior art syringes, and provide a significant advancement in the state of the art.

DETAILED DESCRIPTION OF THE INVENTION

Referring first to FIGS. 1 through 6, a squeeze-actuated syringe 10, in accordance with a first preferred embodiment of the invention, is shown, along with a filled collapsible ampul 12 contained therein, as will be described below. The syringe 10 comprises a rigid, elongate body 14 having a generally convex exterior gripping surface 16 and a generally concave interior surface 18 which forms a receptacle for the ampul 12. The body 14 extends longitudinally between a proximal end and a distal end, with a movable handle 22 being attached by a double-jointed hinge 24 to the distal end. The hinge 24 comprises a proximal joint 26 and a distal joint 28 joined by an articulating segment 30. The handle 22, the hinge 24, and the body 14 may be fashioned, as an integral unit, of a plastic material, such as polycarbonate, polypropylene, or polysulfone. The handle 22 has an outer surface adapted to be manually engaged for the application of pressure thereto, and an integral, longitudinally-extending projection or pad 32, which is thus situated in opposed relationship to the receptacle formed by the interior body surface 18. The underside of the projection or pad 32 thus defines a pressure application surface which is advantageously contoured to conform to the shape of the interior surface 18 of the syringe body 14. The construction of the hinge 24, with its two spacially-separated joints 26 and 28, allows the handle to maintain its longitudinal axis in substantially parallel alignment with the longitudinal axis of the body 14 as the handle is moved toward and away from the body, as will be described below.

Extending upwardly (using the orientation depicted in the drawings) from one side of the body 14, at or near its mid-point, is a first serrated member 34, which is attached to the body 14 by a pair of spaced-apart legs 36 so that a slot 38 is defined between the upwardly-extending serrated member 34 and the body. Extending downwardly from the same side of the handle 24 is a second serrated member 40 which is axially-aligned with the upwardly-extending member 34. The upwardly-extending member is provided with a vertical succession of inwardly-extending serrations or teeth 42 which are engageable with mating, outwardly-extending serrations or teeth 44 arranged in a vertical succession on the downwardly-extending serrated member 40. The two serrated members 34 and 40 are somewhat flexible, so that they can be flexed out of co-engagement, as will be described below, and then spring back into the co-engaging position shown in FIGS. 3, 4, and 5.

As mentioned above, the syringe 10 is designed for use with a collapsible ampul 12 that can be seated in the receptacle formed by the interior surface 18 of the body 14. The ampul 12 is a hollow sack of a resilient plastic material, such as polyethylene, polyvinylchloride, or polyurethane, for example. It can be prefilled with a liquid medicament to be injected, or it can be evacuated and sealed, or it can be unfilled, and unsealed, depending on its application, as will be described further below. For the purposes of the present discussion, it will be assumed that the ampul is filled with a pre-measured volume of liquid, and then sealed.

Figure 1:
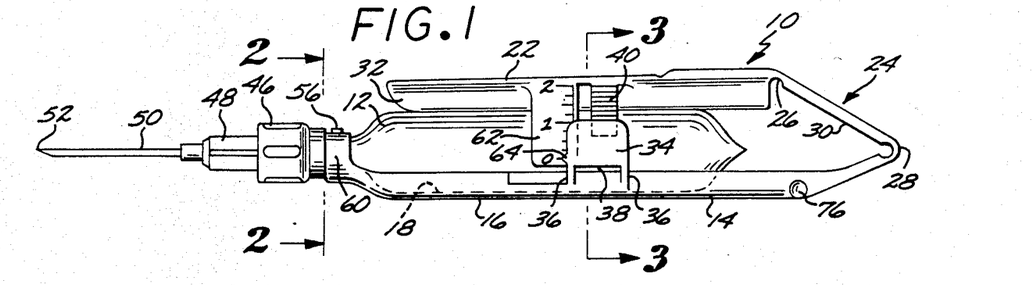
FIG. 1 is a side elevational view of a first preferred embodiment of the invention, showing the syringe with a filled ampul.
Figure 2:
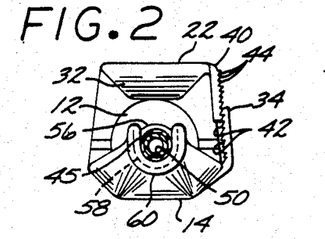
FIG. 2 is a cross-sectional view along line 2—2 of FIG. 1.
Figures 4, 6, 7, 8, 9:
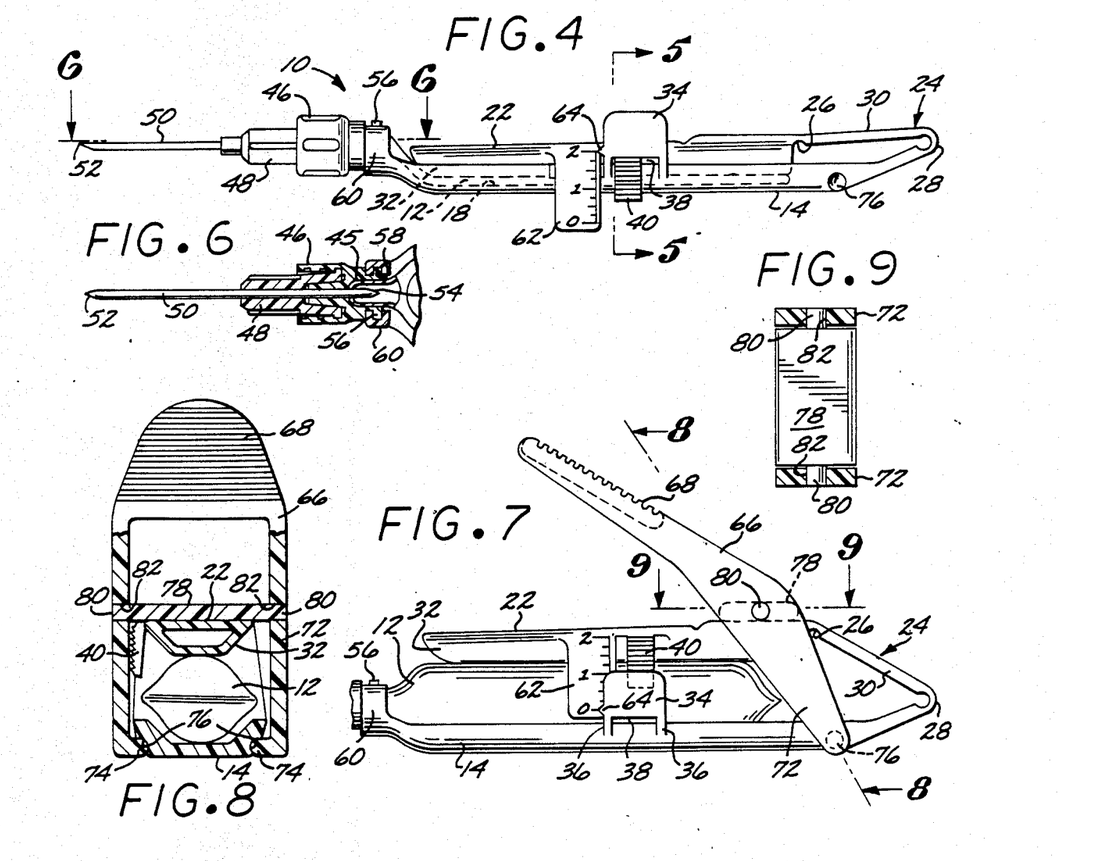
FIG. 4 is a side elevational view of the embodiment of FIG. 1, showing the syringe after the ampul has been compressed to discharge the fluid therefrom.
FIG. 6 is a cross-sectional view along line 6—6 of FIG. 4.
FIG. 7 is a side elevational view of a modified form of the first preferred embodiment, showing the syringe with a filled ampul.
FIG. 8 is a view, partially in cross-section, taken along line 8—8 of FIG. 7.
FIG. 9 is a cross-sectional view along line 9—9 of FIG. 7.

As best shown in FIG. 6, the proximal end of the ampul 12 is formed into a nipple 45. The nipple 45 is held within a fitting 46, preferably of the luer lock type, which, in turn, accommodates a mating fitting 48 on a disposable hypodermic needle 50. The needle 50 is a double-ended needle; extending to a sharply-pointed proximal end 52, and a pointed distal end 54. When the needle fitting 48 is connected to the ampul fitting 46, the distal end 54 of the needle 50 extends distally into the ampul fitting 46 and punctures the nipple 45. The distal end of the ampul fitting 46 has a peripheral flange 56 which seats in an internal groove 58 in a U-shaped collar 60 at the proximal end of the body 14, as shown in FIGS. 2 and 6. In this manner, the ampul 12 and the needle 50 attached to it are firmly supported by the body 14 and restrained from lateral and longitudinal movement relative to the body.

The operation of the first preferred embodiment of FIGS. 1 through 6 will now be easily understood. With the handle 22 lifted away from the body 14, an ampul 12 is seated in the receptacle formed by the interior body surface 18, with the flange 56 of the ampul fitting 46 being seated in the groove 58 of the collar 60. A double-ended needle 50, of the type previously described, is connected to the syringe body 14 and to the ampul 12 via the needle fitting 48 and the ampul fitting 46, as described above. The distal end 54 of the needle 50 thereby ruptures or punctures the ampul nipple 45 to allow the discharge of the ampul's contents through the needle 50.

To perform an injection of the ampul's contents through the needle 50, the handle 22 and the exterior surface 16 of the body 14 are gripped by the user, and the handle 22 is squeezed toward the body, thereby applying pressure to the ampul 12 via the projection or pad 32. The ampul 12 is thereby compressed, discharging its contents through the needle 50. The double-jointed hinge 24, in keeping the axes of the handle 22 and the body 14 in substantially parallel alignment, enhances the uniformity of flow from the ampul, while also facilitating a substantially complete emptying of its contents.

Figure 3:
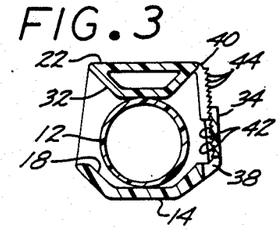
FIG. 3 is a cross-sectional view along line 3—3 of FIG. 1.
Figure 5:
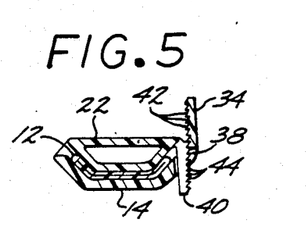
FIG. 5 is a cross-sectional view along line 5—5 of FIG. 4.
Figure 10:
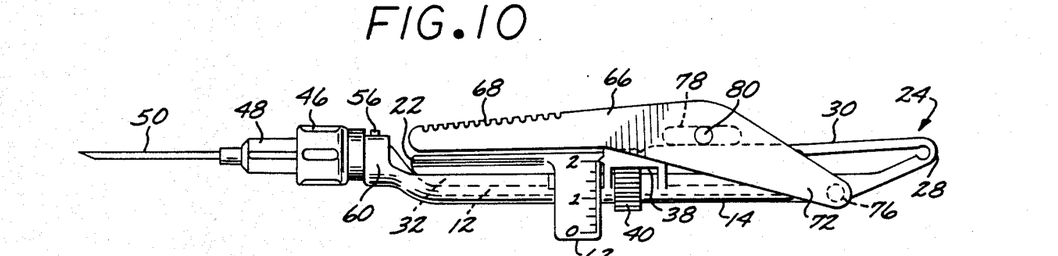
FIG. 10 is a side elevational view of the embodiment of FIG. 7, after the ampul has been compressed to discharge the fluid therefrom.

As shown in FIGS. 3, 4, and 5, the serrated members 34 and 40 provide a ratcheting locking mechanism between the handle 22 and the body 14, with the teeth 42 and 44 providing a plurality of detented positions for the handle relative to the body. Specifically, each of the teeth 42 on the upwardly-extending serrated member 34 may be considered as defining a selectable detented handle position. As previously described, the teeth 44 on the downwardly-extending serrated member 40 are engageable with (or mesh with) the teeth 42, thereby releasably locking the handle into a selected one of these detented positions. As the handle is urged toward the body, the teeth 44 on the handle-borne serrated member 40 sequentially engage successive teeth 42 on the body-borne serrated member 34. At any selected point in the travel of the handle toward the interior surface 18 of the body, the movement of the handle can be stopped, and the teeth 42 and 44 which are co-engaged at that selected position will hold the handle and the body in a fixed position relative to each other until pressure is again applied to the handle to continue its downward motion. By this ratcheting or detented locking mechanism, the ampul can be emptied by a series of discrete, intermittent injections, thereby allowing the volume of the ampul to be metered out intermittently over a period of time. Because the handle is restrained from movement relative to the body between the intermittent injections, back pressure from the patient's body, and/or the resilient "shape memory" of the ampul, cannot decompress the ampul. Thus, the likelihood of aspirating either air or body tissue into the syringe between injections is minimized.

As the ampul 12 is compressed between the pad 32 and the interior body surface 18, the handle-borne serrated member 40 must slide along the body-borne serrated member 34. To this end, the leading edges of the teeth 42 and 44 are sloped. The trailing edges of the teeth 42 and 44 are, on the other hand, substantially flat, allowing little or no sliding of the serrated member 40 in the opposite (upward) direction. When the handle 22 approaches its downward limit of travel (FIGS. 4 and 5) in which the ampul 12 is fully compressed, the handle-borne serrated member 40 passes through the slot 38 underlying the body-borne member 34.

While the receptacle formed by interior surface 18 of the body 14 can accommodate ampuls of widely-differing sizes, it may be desired to manufacture standard syringe sizes for different ampul capacities. In such cases, the handle 22 can be provided with a downward-depending graduated scale 62, located forward of, and oriented substantially parallel to the handle-borne serrated member 40. The scale 62 is marked in units of volume (e.g., cubic centimeters). The body-borne serrated member 34 can then be provided with a pointer 64 which indicates, on the scale 62, how much volume has been discharged from the ampul as the ampul is compressed.

When it is desired to release the handle so that it can be lifted away from the body when the ampul has been partially or completely emptied, one of the serrated members 34 and 40 can be resiliently flexed away from the other, thereby disengaging their respective teeth 42 and 44. The handle can then be lifted completely away from the body, or it can be lifted only part-way to another detented position, and the teeth 42 and 44 simply allowed to re-engage at the newly-selected position. This latter mode of operation will be used, for example, when the syringe is used in aspiration procedures, as will be described below.

FIGS. 7 through 10 illustrate a modified form of the above-described embodiment, in which a detachable auxiliary handle or lever 66 is attached to the regular handle 22 and the distal end of the body 14. The auxiliary handle 66 has an upper portion 68 configured as a gripping surface, and a lower portion 72 having a pair of inwardly-extending pins 74 that are detachably seated in a pair of recesses 76, one on each side of the proximal end of the body 14, as best shown in FIG. 8. The upper portion 68 is formed at an obtuse angle with the lower portion 72, so that the upper portion 68 extends over the regular handle 22 toward the proximal end thereof, forming an acute angle therewith, as shown in FIG. 7. The auxiliary handle 66 is bifurcated into two sides, each detachably connected to one side of the syringe body 14 by a pin 74 seated in a recess 76. The two sides of the auxiliary handle 66 are connected by a transverse pivot plate 78 having a pivot pin 80 extending from each side thereof to be pivotably received in an aperture 82 in each side of the auxiliary handle near the juncture between the upper portion 68 and the lower portion 72. When the auxiliary handle 66 is attached to the body 14, the underside of the pivot plate 78 rests on the top surface of the regular handle 22, just forward of the proximal joint 26 of the hinge 24.

The auxiliary handle 66 allows the user to apply additional leverage to the regular handle 22, with the downward force applied by the user to the upper end 68 being transmitted to the handle 22 through the pivot plate 78. In this manner, the ampul 12 can be compressed more forcefully. Thus, the auxiliary handle 66 may be useful if the ampul contains a relatively viscous liquid to be injected. It may also be of benefit in certain procedures, such as angioplasty, in which the contents of the ampul must be injected into the patient's body under a relatively high pressure. When no longer needed the auxiliary handle 66 is detached from the syringe body by simply removing the pins 74 from the recesses 76.

Figure 11:
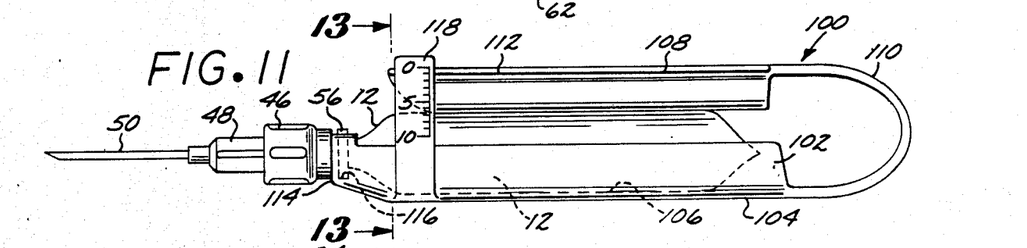
FIG. 11 is a side elevational view of a second preferred embodiment of the invention, showing the syringe with a filled ampul.
Figure 12:
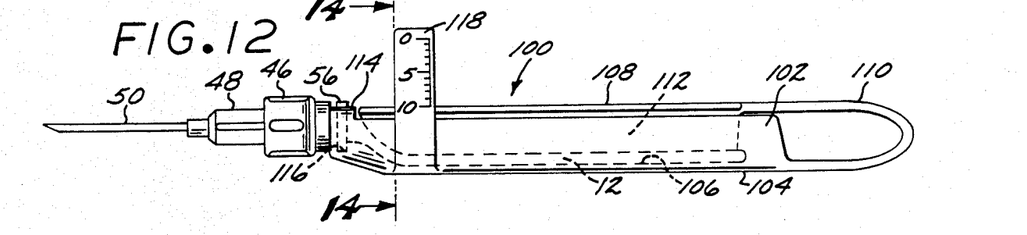
FIG. 12 is a side elevational view of the embodiment of FIG. 11, showing the syringe with an ampul that has been emptied.

FIGS. 11 through 14 illustrate a second preferred embodiment of the invention. In this second embodiment, a syringe assembly 100 comprises a syringe body 102 much like the body 14 of the first embodiment. Thus, the body 102 has an exterior gripping surface 104 and an interior surface 106 forming a receptacle for the ampul 12. A movable handle 108 is attached to the distal end of the body by a hinge 110. The hinge 110 may be of the double-jointed type described above in connection with the first embodiment, or, as shown in FIGS. 11 and 12, it may be an arcuate hinge, in effect a "multi-jointed" hinge. The arcuate hinge 110, like the above-described double-jointed hinge 24, allows the handle to maintain a substantially parallel alignment with the longitudinal axis of the body as the handle is moved toward the body. In all other respects, the handle 108 of the second embodiment is similar to the handle 22 of the first embodiment, including the provision of a projection or pad 112 on its underside for bearing against the ampul 12. Like the first embodiment, the proximal end of the body 102 terminates in a U-shaped collar 114 having an internal groove 116 for seating the ampul fitting 46.

Figures 13, 14:
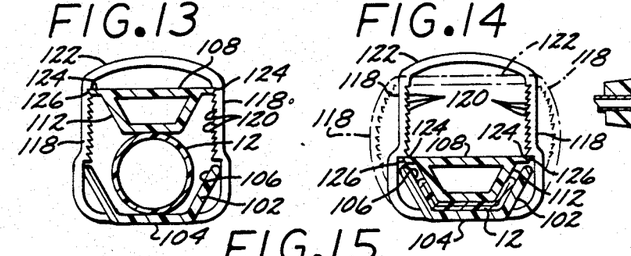
FIG. 13 is a cross-sectional view along line 13—13 of FIG. 11.
FIG. 14 is a cross-sectional view along line 14—14 of FIG. 12.

The second embodiment differs from the first embodiment primarily in the construction of the ratcheting lock mechanism. In the second embodiment, this mechanism comprises an inverted U-shaped structure including a pair of serrated members 118 extending upwardly from the body near the proximal end thereof. The two serrated members 118 are on opposite sides of the body 102, and they each have a vertical array of serrations or teeth 120 facing inwardly in lateral opposition to each other. The upper ends of the two serrated members 118 are joined by a flexible linking member or bridge 122, which, in its normal state, has an upwardly convex shape, as shown in FIGS. 13 and 14. The handle 108 extends between the serrated members 118, with each of its sides extending laterally to form a flange or lip 124 having a tapered edge 126. Each of the lips 124 is engageable with the teeth 120 of the adjacent serrated member 118, with the tapered edge 126 engaging the sloped leading edges of the teeth.

In the compression or injection mode of operation (i.e., the handle 108 being urged toward the body 102 to compress the ampul 12), the ratcheting lock mechanism (members 118 and lips 124) functions similarly to the analogous mechanism of the first embodiment. Thus, as the handle 108 is pressed toward the body, the lips 124 successively engage a pair of opposed teeth 120, each such pair defining a selectable detented position for the handle relative to the body. In this manner, intermittent fractional injections of the ampul's contents can be performed, with the handle being restrained from upward movement between injections by the engagement between the flat upper surfaces of the lips 124 and the flat trailing edges of the teeth 120.

To release the handle to allow it to be lifted away from the body, the top surface of the flexible bridge 122 is pressed downwardly, thereby bowing the serrated members 118 outwardly, as shown in the broken outline in FIG. 14. The bowing of the serrated members 118 disengages the teeth 120 from the lips 124, thereby allowing the handle to be lifted to its starting position (FIG. 13), or to any intermediate detented position. When the handle has been lifted to its selected position, the bridge 122 is released, allowing the resilient serrated members 118 to return to their upright positions, thereby re-engaging the teeth 120 and the lips 124. In this manner, an aspiration function can be performed in a manner similar to that of the first embodiment.

As in the first embodiment, the body of the second embodiment is configured to accept ampuls of widely varying sizes. Alternatively, the syringe 100 can be used only with ampuls of a specified volumetric capacity. In the latter case, a graduated volumetric scale can be marked on one (or both) of the serrated members 118 to indicate the amount of fluid discharged from the ampul, by observing the position of the lips 124 relative to the serrated members 118.

Figure 15:
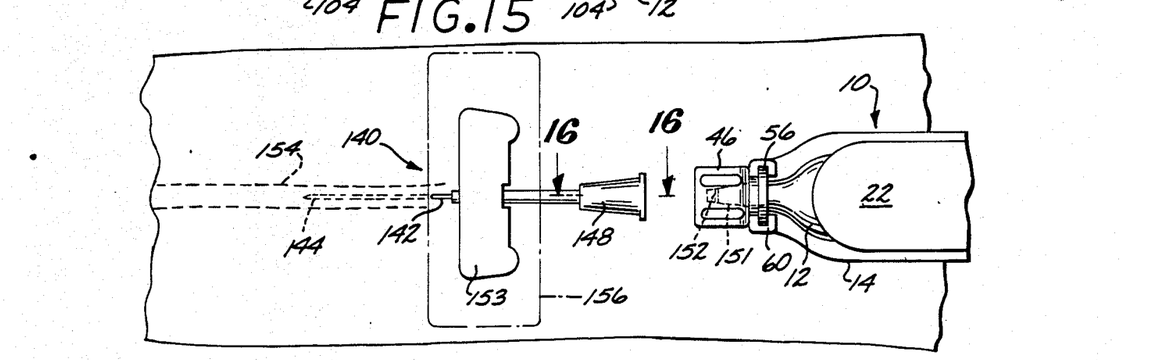
FIG. 15 is a plan view of the proximal portion of a syringe in accordance with a first preferred embodiment, showing its use with an intravenously inserted needle for the purpose of aspirating a blood sample.
Figure 16:
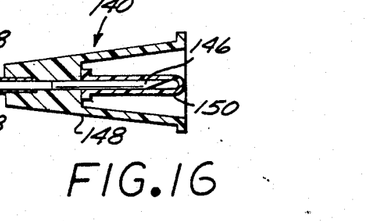
FIG. 16 is a cross-sectional view along line 16—16 of FIG. 15.

FIGS. 15 and 16 illustrate the use of the present invention in its aspiration mode to take a blood sample from a patient. The syringe assembly shown is the syringe assembly 10 in accordance with the first preferred embodiment described above. Nevertheless, the second preferred embodiment can also be used for aspiration, as mentioned above. With either embodiment, aspiration is performed with an evacuated syringe, so the starting position for the handle is the fully compressed position shown in FIGS. 4, 10, 12, and 14. The ampul used can be evacuated and then sealed, or it can be left empty and unsealed. In the latter case, the air in the ampul must, of course, be removed by fully compressing the ampul before the needle is attached to it in the manner described below.

In taking venous blood samples, a special needle assembly 140 is advantageously used. This needle assembly comprises a double-pointed needle 142 having an external point 144 and an internal point 146 extending into the interior of a fitting 148. The fitting 148 may be similar to the needle fitting 48 described previously herein, except that it is provided with a sealing sheath 150 that covers that portion of the needle 142, including the internal point 146, which extends into the interior of the fitting 148. For this application, the ampul fitting 46 has a central cone 151 defining an internal fluid passage which is sealed by a resilient, resealing plug 152.

As shown in FIG. 15, the external needle point 144 is first inserted into the patient's body, into a vein 154, for example. The needle is stabilized by means of a stabilizer strip 153, which may be attached to the patient's skin by a strip of tape 156. At this point in the procedure, the needle assembly and the syringe assembly are, as yet, unconnected, and the internal needle point 146 remains covered by the sheath 150 to prevent the outflow of blood. When a sample is to be drawn, the syringe assembly is attached to the fitting 148 by means of the ampul fitting 46. The seating of the needle fitting 148 into the ampul fitting 46 causes the cone 151 to displace the sheath 150 so as to uncover the internal point 146. The internal needle point 146, in turn, penetrates the plug 152 to establish communication with the ampul.

Once the ampul has been entered by the internal needle point 146, the handle of the syringe assembly can be lifted, in the manner previously described, to aspirate the blood into the ampul in a controlled, modulated manner, either by a gradual but continuous lifting, with the ratcheting lock mechanism disengaged, or by an intermittent lifting, with the lock mechanism intermittently engaged at selected detented positions. When aspiration is completed, the syringe assembly is removed from the needle fitting 148 and the plug 152 reseals the passage in the cone 151 of the ampul fitting 46. The needle sheath 150 resiliently returns to its original position, covering the internal needle tip, thereby allowing multiple samples to be taken without removing the needle.

Aspiration can also be performed from a permanent intravenous injection site by means of a microspike attached to the syringe in place of the needle.

From the foregoing description of the preferred embodiments of the invention, its many advantages will be appreciated. For example, the squeezing action with which injections are made makes the syringe easier to manipulate and more convenient to use than plunger-type syringes. The pivoting action of the handle, whereby the handle remains substantially in parallel alignment with the body as it is moved toward and away from the body, enhances uniformity of flow, while facilitating substantially complete emptying of the ampul. The fittings between the ampul and the needle, and between the ampul and the syringe body, assure rigid support for the needle, while allowing the use of a disposable needle/ampul assembly. The ratcheting lock mechanism provides an effective means for intermittent, metered administrations of the ampul's contents when the syringe is used for injection.

When the syringe is used for aspiration, the locking mechanism affords the practitioner with the ability to control and modulate the withdrawal of fluid, thereby minimizing the risks attendant to the uncontrolled application of a relative vacuum to veins or other organs from which fluid may be drawn. In the aspiration mode, the fastening of the needle fitting to the ampul fitting by means such as a luer lock fitting allows multiple samplings with minimum needle movement, as compared to, for example, the evacuated test tube collection device, in which a sealing stopper must be punctured. Moreover, the opportunities for contamination of the collected sample are minimized because of the lack of the need for a pipette to extract multiple aliquots from the ampul, as well as the lack of lubrication or sealing materials in contact with the collected sample.

While two preferred embodiments, and several modifications of these embodiments, have been describe herein, further modifications may suggest themselves to those skilled in the pertinent arts. For example, the auxiliary handle shown and described in connection with the first embodiment may be readily adapted for use with the second embodiment. The ratcheting lock mechanisms shown and described above may also be modified for a variety of specific applications. Likewise, a variety of fittings for attaching the ampul to the needle and to the syringe body may be devised to make use of syringe assemblies in which the needle is a fixed part of the syringe body or of the ampul, for example. These and other modifications should be considered within the spirit and scope of the present invention, as defined in the claims which follow.

What is claimed is:

1. A syringe for use with a collapsible ampul adapted for attachment to a hypodermic needle, said syringe comprising:
   a body having an exterior surface and an interior surface defining a receptacle adapted to receive said ampul, said body having a proximal end and a distal end;
   pressure application means, operatively connected to the distal end of said body for applying pressure against said ampul received in said receptacle when said pressure application means is squeezed toward said interior surface; and
   pressure-responsive locking means, engageable between said body and said pressure application means, for (a) defining a plurality of selectable positions for said pressure application means relative to said receptacle, and (b) releasably locking said pressure application means in a selected one of said selectable positions;
   whereby said locking means engaged said pressure application means with successive ones of said selectable positions as said pressure application means is squeezed toward said interior surface.

2. The syringe of claim 1, further comprising hinge means, operatively connecting said pressure application means and said body, for maintaining said pressure application means in substantially parallel alignment with the longitudinal axis of said body as said pressure application means is squeezed toward said interior surface.

3. The syringe of claim 1, wherein said locking means comprises:
   first engagement means on said body and defining said plurality of selectable positions; and
   second engagement means on said pressure application means for (a) sequentially engaging and disengaging said first engagement means at successive ones of said selectable positions as said pressure application means is squeezed toward said interior surface, and (b) releasably locking in engagement with said first engagement means at a selected one of said selectable positions when the motion of said pressure application means toward said interior surface is stopped.

4. The syringe of claim 3, wherein said first engagement means includes a serrated member extending from said body toward said pressure application means, each of said selectable positions being defined by a serration on said serrated member, and wherein said second engagement means is releasably engageable with each of said serrations defining one of said selectable positions.

5. The syringe of claim 4, wherein said first engagement means comprises a first serrated member, and wherein said second engagement means comprises a second serrated member extending from said pressure application means toward said body, said first and second serrated members being axially aligned so as to be slidably co-engageable, with the serrations of said second serrated member successively engaging the serrations of said first serrated member as said pressure application means is moved toward said interior surface.

6. The syringe of claim 5, wherein at least one of said first and second serrated members is adapted to be resiliently flexed out of engagement with the other of said serrated members to release said second engagement means from engagement with said first engagement means, thereby allowing said pressure application means to be moved away from said interior surface.

7. The syringe of claim 4, wherein said serrated member is a first serrated member extending from one side of said body, said first engagement means further including a second serrated member extending from the opposite side of said body, with the serrations of said first and second serrated members being laterally opposed to each other across said interior surface, each of said selectable positions being defined by an opposed pair of said serrations, said second engagement means being simultaneously engageable with a selected opposed pair of serrations.

8. The syringe of claim 7, wherein said first and second serrated members are linked by a resiliently flexible connecting member, said connecting member being disposed to resiliently flex said first and second serrated members laterally outwardly upon the application of pressure to said connecting member, the flexing of said first and second serrated members thereby releasing the engagement with said second engagement means.

9. The syringe of claim 2, wherein said pressure application means comprises:
 a longitudinal member operatively connected to the distal end of said body by said hinge means and having a pressure-application surface opposed to said receptacle;
 lever means having a first end pivotably attached to the distal end of said body and a second end extending over said longitudinal member toward the proximal end thereof, said second end being adapted to be manually gripped; and
 a pivot plate, pivotably attached to said lever means between said first and second ends thereof and engaging said longitudinal member, whereby a downward force applied to said upper end is transmitted to said longitudinal member by said pivot plate.

10. The syringe of claim 1, further comprising volume indication means, operatively associated with said pressure application means, for indicating the volume of the contents of said ampul extracted therefrom as said ampul is compressed between said pressure application means and said body when said pressure application means is squeezed toward said interior surface.

11. A syringe, comprising:
 a longitudinal body having a proximal end and a distal end, and adapted to receive a collapsible ampul therein;
 pressure application means, connected to the distal end of said body by a hinge, for compressing said ampul received in said body against said body when said pressure application means is squeezed toward said body, and for allowing said ampul to re-assume its uncompressed shape when said pressure application means is moved away from said body; and
 pressure-responsive, detented locking means, engageable between said body and said pressure application means, for (a) defining a plurality of selectable positions for said pressure application means relative to said body, and (b) releasably locking said pressure application means in a selected one of said selectable positions;
 whereby said locking means engages said pressure application means with successive ones of said selectable positions as said pressure application means is squeezed toward said body.

12. The syringe of claim 11, wherein said locking means comprises:
 first engagement means on said body and defining said plurality of selectable positions; and
 second engagement means on said pressure application means for (a) engaging said first engagement means at selected ones of said selectable positions as said pressure application means is moved relative to said body, and (b) releasably locking said pressure application means in a selected one of said selectable positions when the motion of said pressure application means relative to said body is stopped.

13. The syringe assembly of claim 12, wherein said first engagement means includes a serrated member extending from said body toward said pressure application means, each of said selectable positions being defined by a serration on said serrated member, and wherein said second engagement means is releasably engageable with each of said serrations defining one of said selectable positions.

14. The syringe of claim 13, wherein said first engagement means comprises a first serrated member, and wherein said second engagement means comprises a second serrated member extending from said pressure application means toward said body, said first and second serrated members being axially aligned so as to be slidably co-engageable, with the serrations of said second serrated member successively engaging the serrations of said first serrated member as said pressure application means is moved toward said body.

15. The syringe of claim 12, wherein at least one of said first and second engagement means is adapted to be resiliently flexed out of engagement with the other of said engagement means.

16. The syringe of claim 14, wherein said first and second serrated members can be resiliently flexed so as to disengage the serrations of said first serrated member from the serrations of said second serrated member.

17. The syringe of claim 14, further comprising:

first means, extending from said pressure application means substantially parallel to said second serrated member, defining a volumetric scale; and second means on said first serrated member for indicating on said first means the volume discharged from said ampul as said ampul is compressed.

18. The syringe of claim 13, wherein said serrated member is a first serrated member extending from one side of said body, said first engagement means further including a second serrated member extending from the opposite side of said body, with the serrations of said first and second serrated members being laterally opposed to each other across said body, each of said selectable positions being defined by an opposed pair of said serrations, said second engagement means being simultaneously engageable with a selected opposed pair of serrations.

19. The syringe of claim 18, wherein said first and second serrated members are linked by a resiliently flexible connecting member, said connecting member being disposed to resiliently flex said first and second serrated members laterally outwardly upon the application of pressure to said connecting member, the flexing of said first and second serrated members thereby disengaging said second engagement means from said serrations.

20. The syringe of claim 18, wherein said second engagement means includes a laterally-extending flange on each side of said pressure application means.

21. The syringe of claim 18, wherein at least one of said first and second serrated members is marked with a volumetric scale, whereby the position of said pressure application means relative to said first and second serrated members indicates the volume discharged from said ampul as said ampul is compressed.

22. The syringe of claim 11, wherein said pressure application means comprises:

a longitudinal member operatively connected to the distal end of said body by said hinge and having a pressure-application surface opposed to said body;

lever means having a first end pivotably attached to the distal end of said body and a second end extending over said longitudinal member toward the proximal end thereof, said second end being adapted to be manually gripped; and a pivot plate, pivotably attached to said lever means between said first and second ends thereof and engaging said longitudinal member, whereby a downward force applied to said upper end is transmitted to said longitudinal member by said pivot plate.

* * * * *